(12) United States Patent
Casas Louzao et al.

(10) Patent No.: US 7,700,823 B2
(45) Date of Patent: Apr. 20, 2010

(54) TRANSGENIC ANIMALS EXHIBITING MAJOR DISORDERS RELATED TO ALZHEIMER'S DISEASE

(75) Inventors: Caty Casas Louzao, Barcelona (ES); Patrick Benoit, Paris (FR); Laurent Pradier, Verrieres (FR); Gunter Tremp, Palaiseau (FR); Jean-Michel Itier, Savigny sur Orge (FR); Véronique Blanchard-Bregeon, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/957,311

(22) Filed: Oct. 1, 2004

(65) Prior Publication Data

US 2005/0076400 A1 Apr. 7, 2005

Related U.S. Application Data

(60) Provisional application No. 60/523,397, filed on Nov. 19, 2003.

(30) Foreign Application Priority Data

Oct. 2, 2003 (FR) .................................. 03 11578

(51) Int. Cl.
*A01K 67/027* (2006.01)
*G01N 33/00* (2006.01)
(52) U.S. Cl. ............................................. 800/18; 800/3
(58) Field of Classification Search ..................... 800/8, 800/21, 18, 3
See application file for complete search history.

(56) References Cited

U.S. PATENT DOCUMENTS 6,734,336 B1 * 5/2004 Scott et al. ...................... 800/3

FOREIGN PATENT DOCUMENTS

FR 2798556 2/2004
WO WO 01/20977 * 3/2001

OTHER PUBLICATIONS

Irizarry MC, Soriano F, McNamara M, Page KJ, Hyman BT. Abeta deposition is associated with neuropil changes, but not with overt neuronal loss in the human amyloid precursor protein V717F (PDAPP) transgenic mouse. J Neurosci. 1997, 17(18):7053-9.*
Takeuchi A, Duff K et al., Age-related amyloid beta deposition in transgenic mice overexpressing both Alzheimer mutant presenilin 1 and amyloid beta precursor protein Swedish mutant is not associated with global neuronal loss.Am J Pathol. 2000, 157:331-9.*
Mullins LJ, Mullins JJ. Transgenesis in the rat and larger mammals. J Clin Invest. 1996 ;97(7):1557-60.*
Moreadith RW, Radford NB. Gene targeting in embryonic stem cells: the new physiology and metabolism. J Mol Med. 1997;75(3):208-16.*
Campbell KHS and Wilmut I. Totipotency or multipotentiality of cultured cells:Applications and progress Theriogenology 1997, 47:63-72.*
Rockenstein E, Mallory M, Mante M, Sisk A, Masliaha E. Early formation of mature amyloid-beta protein deposits in a mutant APP transgenic model depends on levels of Abeta(1-42). J Neurosci Res. 2001;66(4):573-82.*
Houdebine LM. Production of pharmaceutical proteins from transgenic animals. J Biotechnol. 1994;34(3):269-87.*
Leutner S, Czech C, et al., Reduced antioxidant enzyme activity in brains of mice transgenic for human presenilin-1 with single or multiple mutations. Neuroscience Letter 2000, 292(2):87-90.*
Houdebine et al, 2000, Transgenic Research 9, 305-320.*
Sigmund, C., 2000 Arterioscler. Thromb. Vasc. Biol., 20(6):1425-9.*
Wolfer et al Trends in Neuroscience, 25(7): 336-340, 2002.*
Strunk et al, Genetics, 167: 1821-1832, 2004.*
Shioi et al J Neurochem. 2007;101(3):674-81.*
Schoonjans et al Stem Cells. 2003;21(1):90-7.*
Moussaoui et al Society for Neuroscience Abstracts, (1999) vol. 25, No. 1-2, pp. 1046, poster No. 426.7.*
Casas et al Neurobiology of Aging, (Jul.-Aug. 2002) vol. 23, No. 1, S216.*
Andra et al., 1996, Neurobiology of Aging, 17: 183-190.*
Carlson et al Human Molecular Genetics, 1997, 6: 1951-1959.*
Hsiao et al Neuron, 1995, 15: 1203-1218.*
Chishti, et al Journal of Biological Chemistry, 2001, 276: 21562-21570.*
Krezowski et al Hum Mol Genet. 2004 15;13(18):1989-97.*
Seabrook, Neuropharmacology 1999, 38(1) 1-17.*
Lehman et al Hum Mol Genet. Nov. 15, 2003; 12(22):2949-56.*
Duff et al Briefing in Functional Genomics and Proteomics, 2004, 3, 47-59.*
Rutten et al Society for Neuroscience Abstract Viewer and Itinerary Planner, 2002, vol. 2002, pp. Abstract No. 32nd Annual Meeting of the Society for Neuroscience. Orlando, Florida, USA. Nov. 2-7, 2002.*
Wirths et al Brain Pathology, 2002, 12 (3), 275-286.*

* cited by examiner

*Primary Examiner*—Deborah Crouch
*Assistant Examiner*—Anoop Singh
(74) *Attorney, Agent, or Firm*—Ann Marie Szczepanik

(57) ABSTRACT

The present invention relates to nonhuman transgenic animals exhibiting major disorders related to Alzheimer's disease. The animals can be used for demonstrating compounds intended for the treatment of Alzheimer's disease.

3 Claims, 8 Drawing Sheets

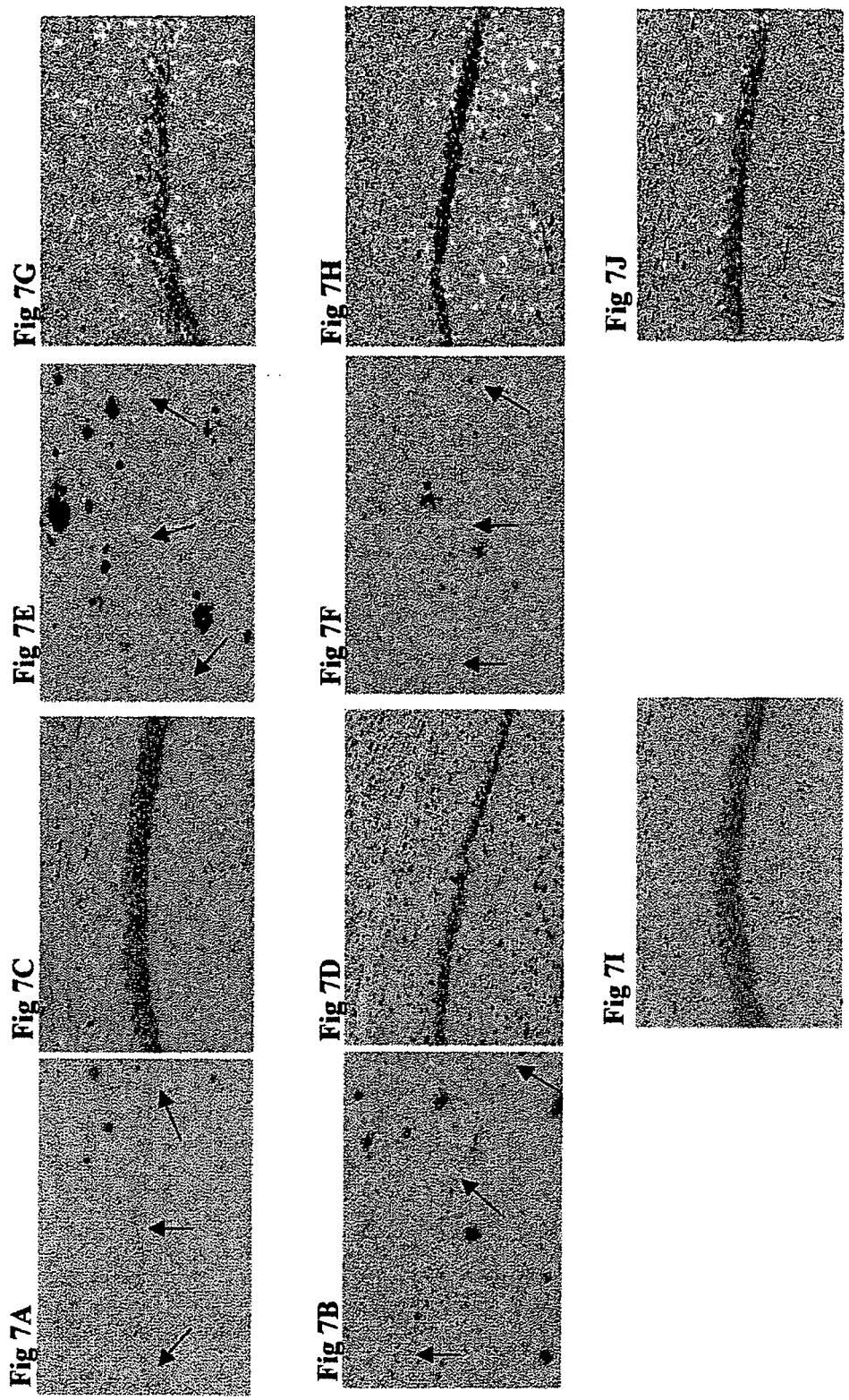

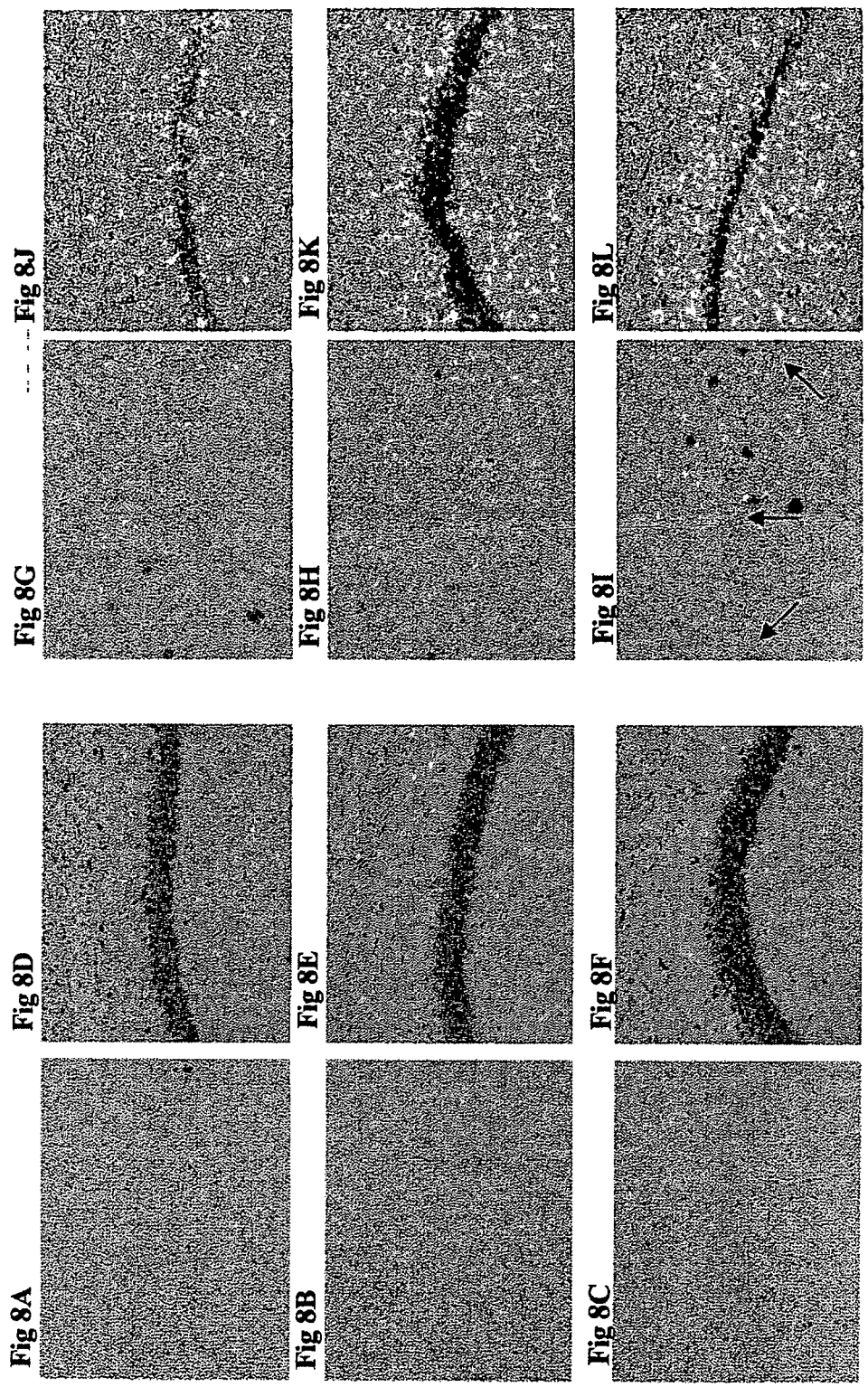

TRANSGENIC ANIMALS EXHIBITING MAJOR DISORDERS RELATED TO ALZHEIMER'S DISEASE

Figures 1A, 1B, 1C:
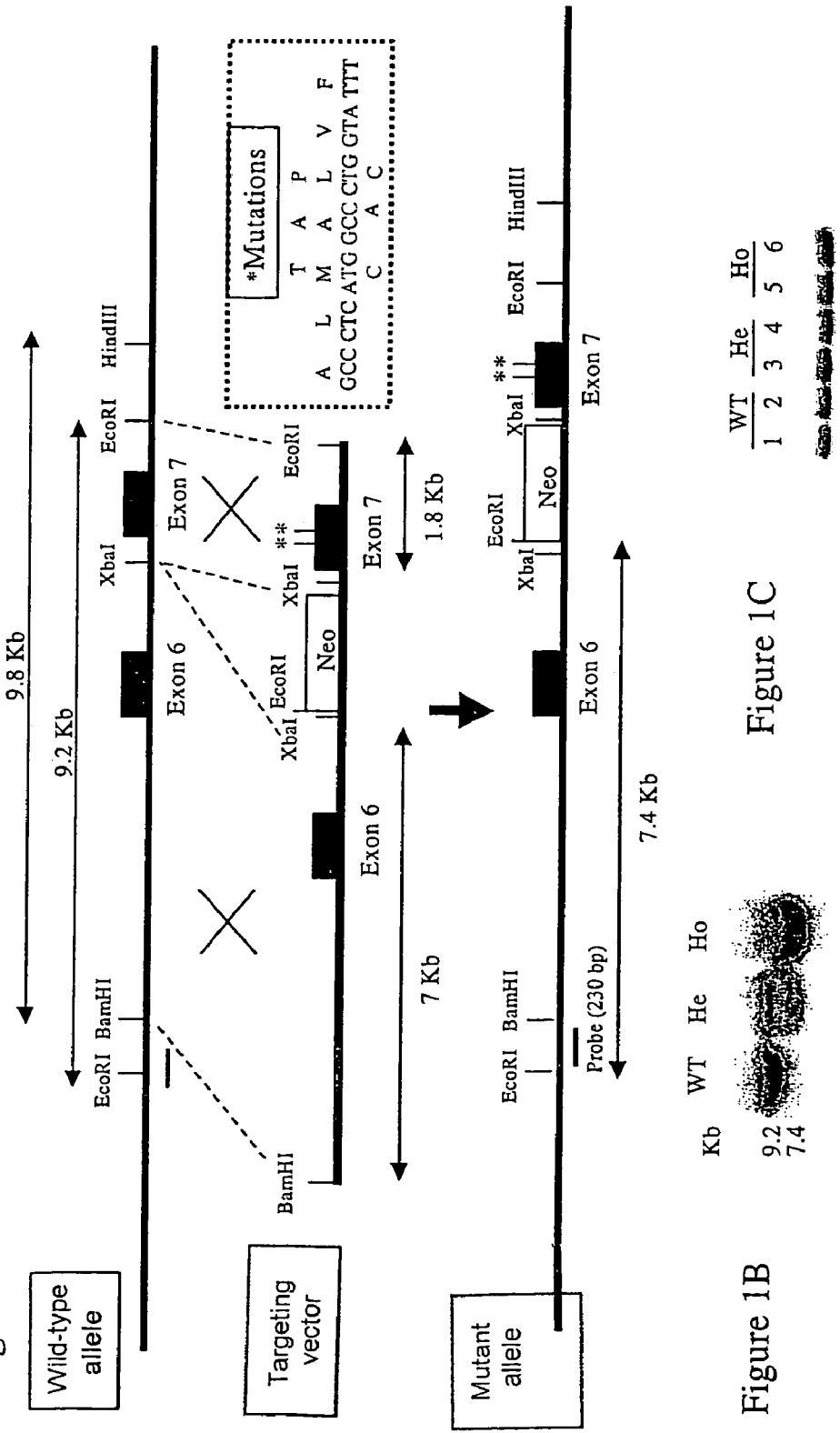

This application claims priority form U.S. provisional application No. 60/523,397 filed on Nov. 19, 2003, which claims priority to application filed in France 0311578, filed on Oct. 2, 2003.

The present application relates to transgenic animals which are models of Alzheimer's disease (AD). It also relates to the use of these animals.

Alzheimer's disease is a progressive neurodegenerative disease which affects a large proportion of the elderly population. This disease is characterized in clinical terms by a loss of memory and a decline in cognitive functions and, in neuropathological terms, by a pronounced loss of neurones and the presence in the brain of intracellular neurofibrillar deposits and of extracellular deposits of β-amyloid peptide (Aβ) forming amyloid plaques.

Amyloid plaques are mainly made up of Aβ peptides containing 40 or 42 residues, which are generated during the proteolytic process for the Aβ peptide precursor (APP). The extracellular deposits of Aβ are very specific for disorders related to Alzheimer's disease. They represent the early and invariable characteristic of all forms of Alzheimer's disease, including the familial forms (FAD). The familial forms appear relatively early (between 30 and 60 years old) and are due to mutations in the APP gene in 5% of FAD cases, with eight single or double missense mutations identified, in the presenilin 1 (PS1) gene in 50 to 70% of FAD cases, with more than 100 different mutations identified to date, and in the presenilin 2 gene in more rare FAD cases, with two missense mutations described. It has been shown that mutations in these three genes induce changes in the proteolysis of APP, which lead to an overproduction of Aβ, especially of the long form Aβ42, and to the early appearance of the pathological conditions and of symptoms similar to those of the sporadic forms of Alzheimer's disease.

Animal models intended to represent certain characteristics of the pathology of Alzheimer's disease have already been described in the literature.

They are, firstly, transgenic mice carrying mutations in the APP gene. They develop pathological conditions similar to Alzheimer's disease from one year old. Thus, the PDAPP mouse, overexpressing human APP carrying the mutation V717F, develops Aβ deposits in the brain with age, but shows no neuronal loss beyond the positioning of the plaques themselves (Irizarry et al., 1997, J.Neurosc. 17(18): 7053-7059). This phenomenon will be referred to as "plaque effect".

Similarly, the Tg(HuAPP695. K670N-M671L)2576 mouse, expressing the human isoform APP K670N-M671L (APPSw for Swedish mutation), exhibits amyloid-type deposits but shows no neuronal loss (Irizarry et al., 1997, J. Neuropathol. Exp. Neurol 56: 695-973).

In a study by Calhoun et al. (1998, Nature 395: 755-756), a neuronal loss was shown in certain brain regions in the vicinity of the amyloid plaques, in APP23 transgenic mice 14-18 months old expressing a mutated isoform of human APP. This observation is controversial since the loss is small and occurs in relatively old animals and especially in the vicinity of plaques, which might correspond to the previously observed "plaque effect". In addition, it is not mentioned, or hardly at all, in a recent commentary which underlines that current animal models do not exhibit complete similarity with all the known characteristics of the pathological conditions of Alzheimer's disease, inter alia the neuronal loss (Trojanowski, 2002, Am.J. Pathol.160: 409-411).

Furthermore, transgenic mice carrying mutations in the PS1 gene are known. They do not appear to develop any pathological condition of Alzheimer's disease type, but exhibit a high amount of Aβ42 peptide (twofold increase compared to wild-type PS1) which is recognized as being highly pathogenic.

In addition, in the transgenic animal models described which carry FAD mutations P264L or M146L in the mouse PS1 gene ("knock-in"), the mutated PS1 protein is not stably expressed (Siman et al., 2000, J.Neurosci., 20: 8717-8726; Flood et al., 2002, Neurobiol. Aging 23: 335-348; Rozhmahel et al., 2002, 23: 187-194). These mice also exhibit a high amount of Aβ42 peptide.

Due to the role of the PS1 protein in the formation of the Aβ42 forms, double transgenic mice carrying mutations in the APP and PS1 genes have also been produced. Like the single transgenics described above, these mice exhibit Aβ deposits but exhibit no neuronal loss (Takeuchi et al., 2000, Am.J.Pathol. 157: 331-339).

Thus, the existing animal models of Alzheimer's disease are not satisfactory since they fail to reproduce a neuronal loss which is, however, a major characteristic of neurodegenerative diseases, including Alzheimer's disease.

The applicant has therefore endeavoured to produce animals exhibiting major characteristics of Alzheimer's disease, including neuronal loss.

It has shown that it is possible to obtain such animals by introducing specific mutations into the gene encoding the PS1 protein in mice, and by crossing them with mice overexpressing the human APP gene.

A first aspect of the invention therefore concerns a nonhuman animal exhibiting, advantageously in its genome, at least one nucleic acid sequence encoding presenilin 1 carrying at least one of the two mutations corresponding to the mutations M233T and L235P on the mouse PS1 protein.

Advantageously, such an animal carries both mutations.

Preferably, the PS1 protein carrying the mutations M233T and L235P is of murine origin.

Particularly preferably, the mutated presenilin 1 protein is endogenous.

Thus, an animal according to the present invention advantageously produces a protein comprising the sequence SEQ ID NO: 2. It preferably produces a protein having the sequence SEQ ID NO: 3. It advantageously comprises in its genome the nucleic acid sequence SEQ ID NO: 1 or the sequence SEQ ID NO: 8.

The sequences SEQ ID NO: 1, SEQ ID NO: 2 and SEQ ID NO: 8 result respectively from mutations introduced into the wild-type sequences SEQ ID NO: 4, SEQ ID NO: 5 and SEQ ID NO: 9. The sequence SEQ ID NO: 5 is that of residues 229 to 237 of the mouse wild-type presenilin 1 protein. The sequence SEQ ID NO: 9 is that of the wild-type exon 7 of the mouse gene encoding the presenilin 1 protein, i.e. nonmutated.

Advantageously, an animal according to the present invention coexpresses APP, preferably human APP. Such a gene may comprise one or more FAD mutations. Thus, the mutations in the APP gene may be one of the various mutations described to date in the literature. The mutations in the APP gene may be chosen from the "Swedish" (S), "London" (L) and "Dutch" (D) mutations, alone or in combination.

These mutations are well described in the literature and are characterized in general by the following modifications:

| Nature and position | Swedish mutation | Dutch mutation | London mutation |
|---|---|---|---|
| with respect to APP770 | K 670 N and M 671 L | E 693 Q and/or A 692 G | V 717 I |
| with respect to APP751 | K 651 N and M 652 L | E 674 Q and/or A 673 G | V 698 I |
| with respect to APP695 | K 595 N and M 596 L | E 618 Q and/or A 617 G | V 642 I |
| with respect to the A-β peptide (A42) | | E 22 Q and/or A 21 G | V 46 I |

Also included in the London mutation are all the substitutions other than with isoleucine which are located at position 717 with respect to APP770, such as, for example, the mutations V 717 G and V 717 F.

It is understood that the APP which can be used in the context of the invention may be in various isoforms, and in particular in the forms 695, 751 and 770 or in a truncated form, such as, for example, the isoform APP99, excluding the Swedish mutation for the latter.

Advantageously, said animal also comprises, advantageously in its genome, a nucleic acid sequence encoding all or part of the gene encoding APP751. Advantageously, the APP751 protein is of human origin. It preferably exhibits the mutations K670N and M671L (Swedish) and V717I (London).

In the context of the present invention, the APP gene is advantageously placed under the control of sequences which allow strong expression thereof in neurones, and in particular of transcription-promoting sequences, such as an exogenous promoter. By way of promoter sequences, mention may most particularly be made of the HMG promoter (Gautier et al. (1989), Nucleic Acids Res 17: 20, 8389), and also the PDGF promoter (Sasahara et al. (1991), Cell 64, 217-27), the Thy-1 promoter (Luthi et al. (1997), J Neurosci 17, 4688-99) and the Prion gene promoter (Scott et al. (1992), Protein Sci 1, 986-97).

According to a particularly advantageous embodiment of the invention, the animal model comprises the APP gene having the S, D and/or L mutations, placed under the control of the Thy1 promoter.

Thus, an animal according to the present invention preferably produces a protein comprising the sequence SEQ ID NO: 7. It may exhibit the nucleic acid sequence SEQ ID NO: 6.

Preferably, it is a transgenic mouse derived from crossing between a transgenic mouse ThyAPP (TG53) carrying a nucleic acid sequence encoding the human protein APP751SL and a transgenic mouse carrying a nucleic acid sequence encoding the mouse PS1 protein carrying the mutations M233T and L235P.

The animals according to the present invention reproduce, for the first time, one of the most important characteristics of neurodegenerative diseases, which is early neuronal loss.

They show, moreover, the other characteristics conventionally described for these pathological conditions. The animals exhibit accelerated depositing of amyloid plaques, clearly visible from 2 months of age, and notably so from 6 months of age.

They also exhibit a ratio of the forms Aβ42 to total Aβ, Aβ42/Aβ, of greater than approximately 0.9, from 2½ months old. Such a ratio is very high compared to that described in the literature for other transgenic mice.

The neuronal loss, which is already visible in 6-month-old mice, is clearly pronounced at 10 months.

PKR (Double strand RNA-dependent Protein Kinase) is a stress-activated kinase which phosphorylates eIF2, involved in apoptosis.

PKR is detected in the hippocampus (the structure where the neuronal loss takes place) of 10-month-old APPxPS1KI mice according to the invention. It is not detected in the hippocampus of 12-month-old APPxPS1M146L transgenic mice in which, moreover, no neuronal loss is observed.

The novel characteristics of the animals according to the present invention make them study models which are more complete and representative of the disorders observed in patients suffering from Alzheimer's disease, than those already described. These animals are therefore particularly suitable for demonstrating the neuroprotective properties of compounds intended for the treatment of neurodegenerative diseases, preferably Alzheimer's disease.

Preferably, the animals according to the present invention have the mutant alleles of ps1 in the homozygous state and those of APP in the heterozygous state. However, the same characteristics of said animal can be described in an animal having one of the two mutated ps1 alleles in the heterozygous state and those of APP in the heterozygous state, with, however, a phenotype which is less marked or which appears later.

Another advantage of the animals according to the present invention is that the amount of mutated PS1 protein expressed by this transgenic mouse is equivalent to the amount of endogenous PS1 protein normally expressed by a normal (nontransgenic) mouse, expressing a nonmutated PS1. This characteristic makes it an advantageous study model—without overexpression of the PS1 protein—for demonstrating compounds intended for the treatment of neurodegenerative diseases.

These compounds may in particular be compounds which have an action on the regulation of the PS1 gene at the transcriptional, post-transcriptional, translational or post-translational level, or on the PS1 protein itself by modifying or regulating one or more of its properties, or which have a similar action on the interaction partners or the targets of the PS1 protein, or as compounds which have an action on the regulation of APP and, more broadly, any molecules downstream of the signals initiated by PS1 and APP during the neurodegenerative process.

In the context of the present invention, the animals are advantageously mammals, such as rodents. In particular they are a mouse, a rat or a rabbit.

The mice and the constructs for obtaining them are obtained by methods known to those skilled in the art.

They may be obtained according to conventional transgenesis techniques. By way of example illustrating one of the methods of transgenesis, mention may be made of the method of electroporation of a gene construct containing the modified genes into mouse embryonic stem cells and, after selection, transfer of the cells carrying the desired genetic event into a recipient blastocyst, as described in the examples. In this regard, the mutated PS1 animals according to the invention are obtained by electroporation of an expression cassette comprising a nucleic acid.

Preferably, this nucleic acid is a DNA which may be a genomic DNA (gDNA) or a complementary DNA (cDNA).

The modification of the genome may be the result of an alteration or a modification of one or more genes by "knock-in". This modification may be due to the action of conventional altering or mutagenic agents or else perhaps carried out by site-directed mutagenesis. In the present invention, as regards the mutated ps1 gene, it preferably involves a homologous recombination with a targeting vector carrying the transgene mutated beforehand by site-directed mutagenesis as described in the examples which follow.

The animals expressing the mutated APP protein are obtained by microinjection of a gene construct into the nucleus of a zygote.

The double transgenic animals are obtained by crossing mutated ps1 animals and mutated APP animals.

The animals according to the present invention may advantageously be used for demonstrating the neuroprotective properties of compounds intended for the treatment of neurodegenerative diseases, and preferably Alzheimer's disease. These compounds may be chemical molecules, peptide or protein molecules, antibodies, chimeric molecules and also antisense RNAs or ribozymes. The compounds demonstrated may be used as medicinal products, as they are or in combination with a pharmaceutically acceptable vehicle in order to obtain a pharmaceutical composition. They may in particular be isotonic, sterile saline solutions (monosodium or disodium phosphate, sodium, potassium, calcium or magnesium chloride, etc., or mixtures of such salts), or dry, in particular lyophilized, compositions which, through the addition, where appropriate, of sterilized water or of physiological saline, make it possible to constitute injectable solutes. The injections may be given stereotactically, topically, orally, parenterally, intranasally, intravenously, intramuscularly, subcutaneously, intraocularly, transdermally, etc.

Another subject of the invention therefore relates to a method for demonstrating compounds intended for the treatment of neurodegenerative diseases, comprising at least the following steps:
  administering the test compound or a mixture of test compounds to animals according to the present invention, and
  observing the evolution of one or more characteristic markers reproducing the neuropathology observed in humans.

Another subject of the invention relates to a method for demonstrating compounds intended for the treatment of neurodegenerative diseases, comprising at least the following steps:
  bringing cells extracted from the animals according to the present invention into contact with a compound or a mixture of compounds, and
  measuring the effect(s) of the compounds on whole cells, in cell homogenates or on a subcellular fraction.

Another subject of the invention relates to any biological product derived from one of the two animals of the invention, and also to their uses for demonstrating compounds intended for the treatment of neurodegenerative diseases, preferably Alzheimer's disease. The term "biological product" means in particular cells, protein extracts, DNA, RNA or else antibodies.

Thus, a subject of the present invention is cells or cell lines derived from an animal as described above, in particular embryonic stem cells.

A subject of the invention is also a mouse PS1 protein carrying the amino acid mutations M to T, and L to P, respectively at positions 233 and 235. Advantageously, such a protein comprises the sequence SEQ ID NO: 2. Preferably, it has the sequence SEQ ID NO: 3.

Another subject of the present invention is a nucleic acid encoding the mouse PS1 protein carrying the amino acid mutations M to T, and L to P, respectively at positions 233 and 235.

Advantageously, such a nucleic acid according to the claim comprises the sequence SEQ ID NO: 1 or the sequence SEQ ID NO: 8.

A subject of the present invention is also the sequences complementary to these nucleic acids and vectors comprising these nucleic acids or the sequences complementary thereto.

Another aspect of the invention concerns the use of these proteins for demonstrating the neuroprotective properties of compounds intended for the treatment of neurodegenerative diseases.

The present invention is illustrated by the following examples, without it being limited, however, to only these examples.

In these examples, the results described demonstrate the advantage of the PS1KI mice and clearly support the preferred use of the PS1KIxAPP model in therapeutic strategies since it has the advantage of representing the main characteristics of the neurodegenerative diseases known to date.

FIGURE LEGENDS

FIG. 1 A: Diagrammatic representation of the structure of the murine ps1 gene and of the main restriction sites around the wild-type exon 7 (upper line) and the targeting vector used (middle line). The nucleotide base changes to generate the codon mutations M233T and L235P, mutations in exon 7 (*), are represented in the dotted frame. The mutated allele PS1KI containing the neomycin (Neo) resistance cassette is represented on the lower line. The position of the 230 bp probe used to identify the newborns is also indicated.

FIG. 1 B: Southern blot using the 230 bp probe to distinguish the wild-type WT alleles (band at 9.2 kb) and the heterozygous PS1KI (He, double band) and homozygous PS1KI (Ho band at 7.4 kb) alleles in various mice.

FIG. 1 C: Immunoblot of the C-terminal fragment of PS1 showing that the levels of expression of the PS1 protein are not altered by the presence of the mutations of the PS1KI allele.

Figure 2A:
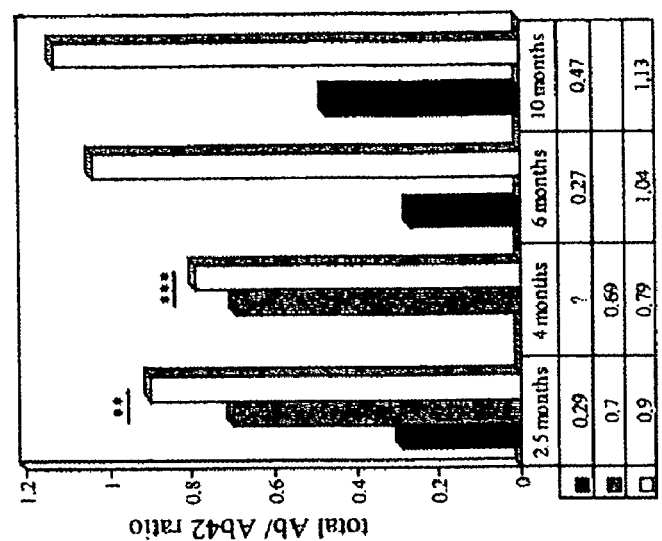
Figure 2B:
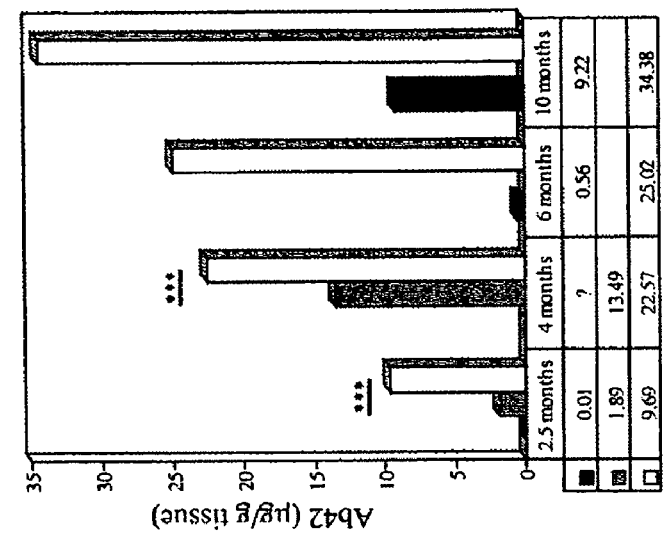
Figure 2C:
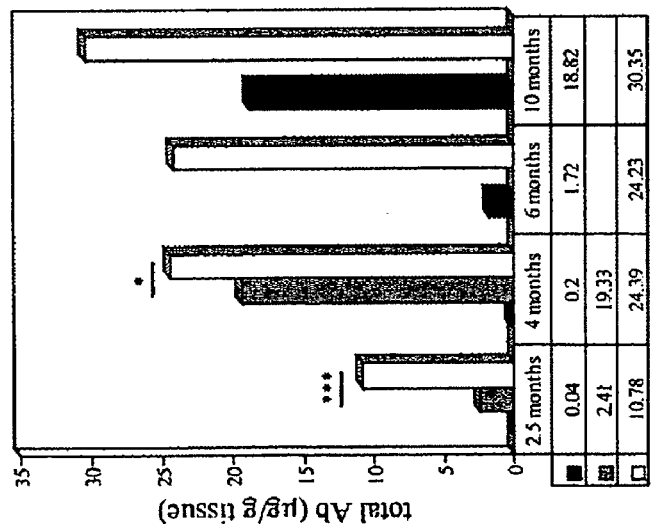
Figure 3A:
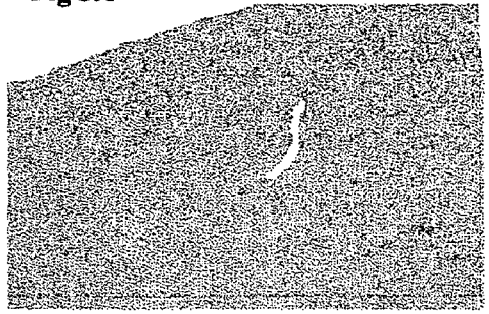
Figure 3D:
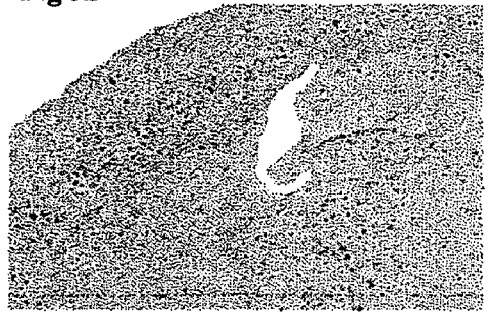
Figure 3B:
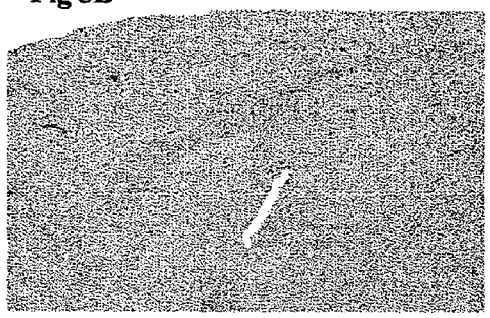
Figure 3E:
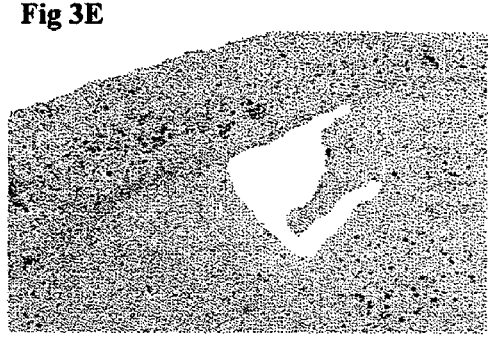
Figure 3C:
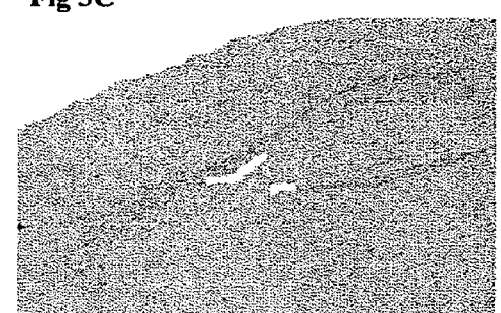
Figure 3F:
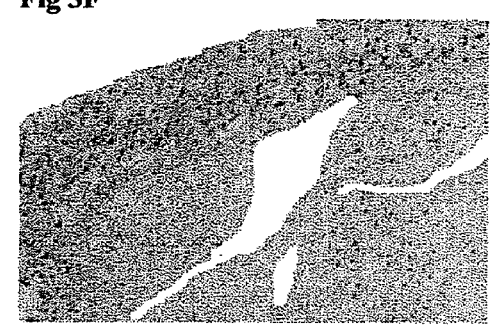
Figure 4A:
Figure 4B:
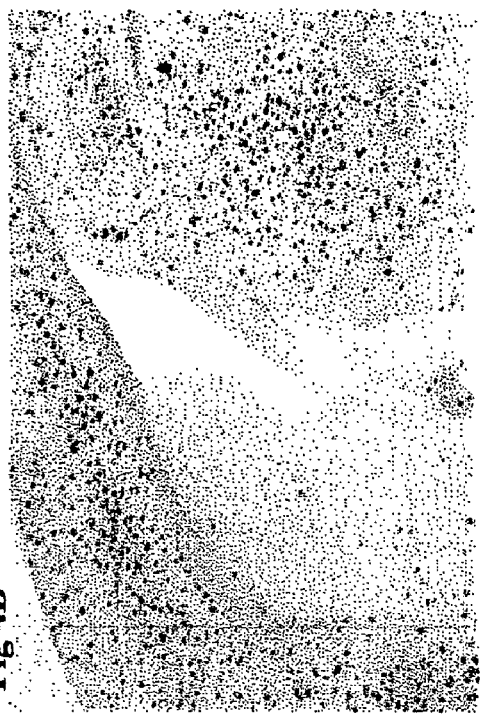
Figure 4C:
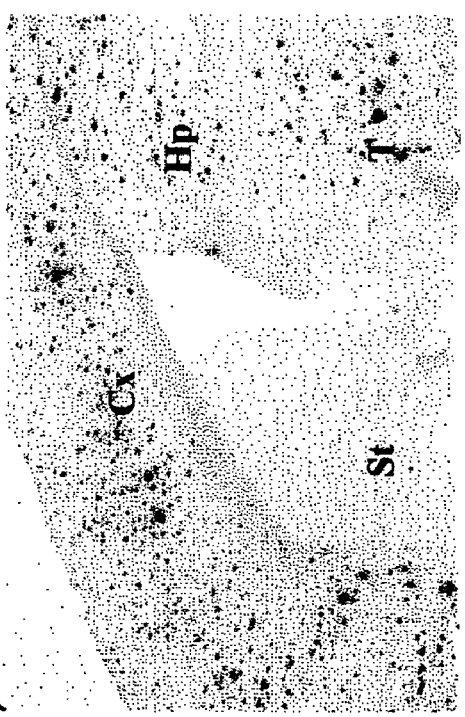
Figure 4D:
Figure 5A:
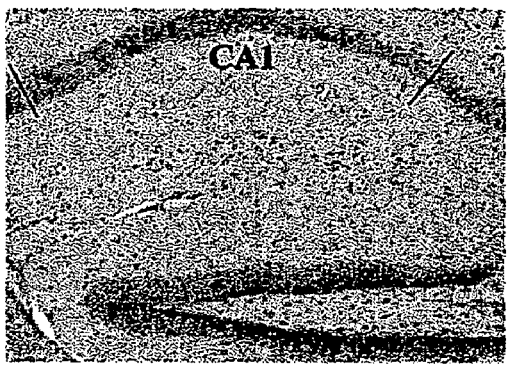
Figure 5B:
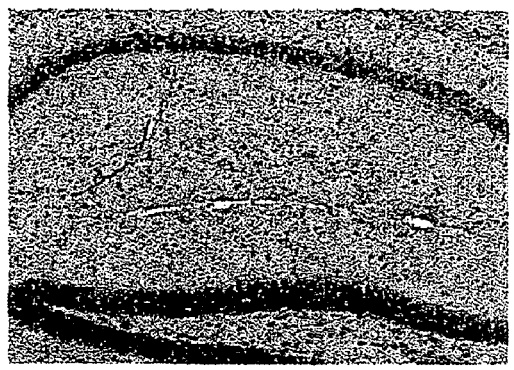
Figure 5C:
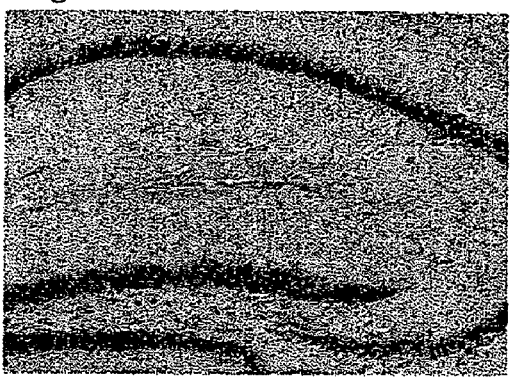
Figure 5D:
Figure 5E:
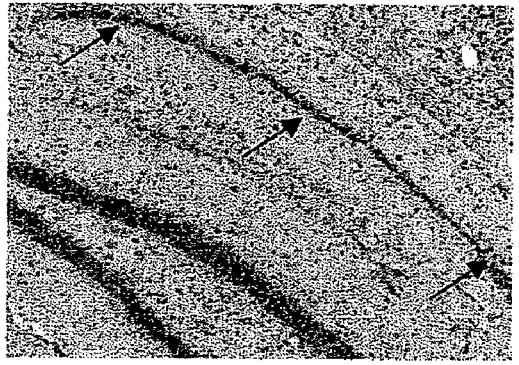
Figure 5F:
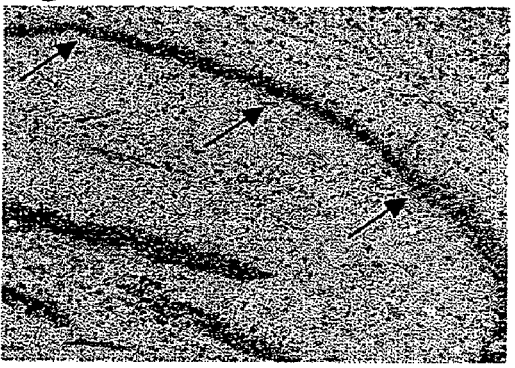
Figure 6E:
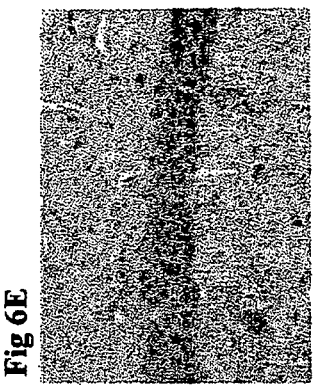
Figure 6F:
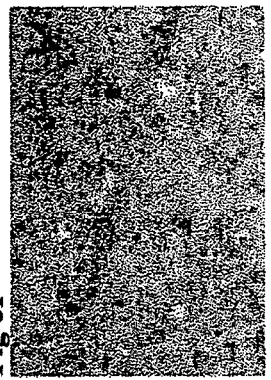
Figure 6B:
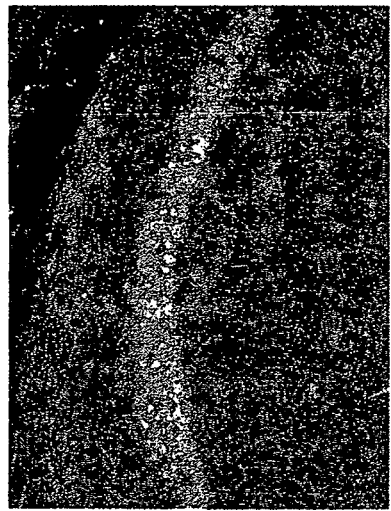
Figure 6D:
Figure 6A:
Figure 6C:
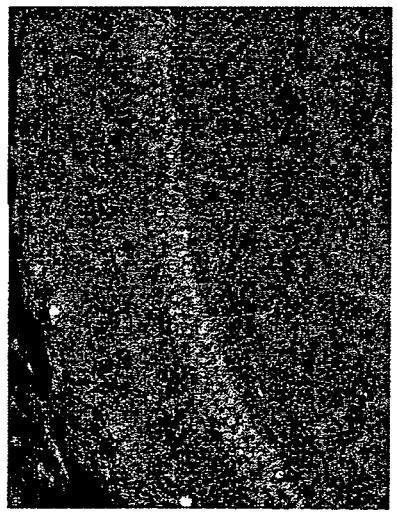

FIGS. 2A, 2B and 2C: Quantification, respectively, of total Aβ, of Aβ42 and of the total Aβ/Aβ42 ratio, at 2.5, 4, 6 and 10 months old.

FIG. 3: Acceleration of the process of deposition of the Aβ peptide in the APP751SLxPS1KI Ho mice. Plate illustrating the regional distribution of the extracellular deposits of the Aβ peptide in the brain at 6 months. The images represent the Aβ immunolabeling (Ab 4G8) in 3 APP751SL mice (FIGS. 3A, 3B and 3C) and 3 APP751SLxPS1KI Ho mice (FIGS. 3D, 3E and 3F). The immunolabeling demonstrates the appearance at 6 months of the first deposits, which are still rare, in the cortex (Cx) and in the hippocampus (Hp) of the APP751SL mice. In comparison, in the APP751SLxPS1KI Ho mice of the same age, the number of deposits is greatly increased in these regions. It should be noted that, in these mice, deposits are already present in notable amount in the thalamus (T).

FIG. 4: Progression with age of the process of deposition of the Aβ peptide. Plate illustrating the regional distribution of the Aβ deposits in the brain at 10 months. The images correspond to 2 APP751SL mice (FIGS. 4A and 4B) and 2 APP751SLxPS1KI Ho mice (FIGS. 4C and 4D). In the APP751SL mice, the immunolabeling demonstrates a considerable increase in the number and in the size of the deposits in the cortex (Cx) and the hippocampus (Hp) at 10 months, compared to 6 months of age, and the appearance of the first deposits in the thalamus (see FIG. 3). The density and the size of the deposits are also greater at 10 months in the cortex, the hippocampus and the thalamus of the APP751SLxPS1KI Ho mice. It should be noted that, in these mice, a small number of deposits can be detected in the striatum (St).

FIG. 5: Process of neuronal death in CA1 in the APP751SLxPS1KI Ho mice. Plate illustrating affected pyramidal neurones in the hippocampus of 10-month-old APP751SLxPS1KI Ho mice. The images represent Cresyl violet staining, at low magnification, in the hippocampus in 2 PS1KI Ho mice (FIGS. 5A and 5B), 2 APP751SL mice (FIGS. 5C and 5D) and 2 APP751SLxPS1KI Ho mice (FIGS. 5 E and 5F). The density and the thickness of the pyramidal cell layers in the hippocampus are qualitatively comparable in the 10-month-old APP751SL mice and PS1KI Ho mice. On the other hand, at the same age, they are clearly decreased in the APP751SLxPS1KI Ho mice, in particular in layer 1 of Ammon's horn (CA1). It should be noted that the number of small cells stained blue (glial type cells) appears to be increased in the hippocampus of the APP751SLxPS1KI Ho mice.

FIG. 6: Process of neuronal death in CA1 in the APP751SLxPS1KI Ho mice. Plate illustrating affected neurones in CA1 at 10 months old via the use of other neuronal markers, methyl green and BIP immunolabeling. The images represent the methyl green staining, at high magnification in CA1, in a nontransgenic mouse (FIG. 6A), a PKS1KI Ho mouse (FIG. 6B), an APP751SL mouse (FIG. 6C) and an APP751SLxPS1KI Ho mouse (FIG. 6D). They represent the BIP immunolabeling at high magnification in CA1, in a PS1KI Ho mouse (FIG. 6E) and an APP751SLxPS1KI Ho mouse (FIG. 6F). Compared to the nontransgenic, PS1KI Ho and APP751SL mice, the number of neuronal cells stained with methyl green is clearly decreased in the CA1 region of the APP751SLxPS1KI Ho mouse. The detection of a considerable number of stained glial type cells in the hippocampal parenchyma of this double transgenic mouse should be noted. The BIP immunolabeling also confirms the considerable loss of pyramidal neurones in CA1 in the 10-month-old APP751SLxPS1KI Ho mouse.

FIG. 7: Neuronal death in CA1 and intracellular deposition of the Aβ peptide. Plate illustrating the two pathological processes, affected neurones and abnormal intracerebral accumulation of the Aβ peptide at 10 months old. The images represent, at high magnification in CA1, the Aβ immunolabeling in 2 APP751 mice (FIGS. 7A and 7B) and 2 APP751SLxPS1KI Ho mice (FIGS. 7E and 7F). They represent, at high magnification in CA1, the Cresyl violet staining in the APP751 mice (FIGS. 7C and 7D), the APP751SLxPS1KI Ho mice (FIGS. 7G and 7H) and 2 PS1KI Ho mice (7I and 7J). At 10 months old, both in the single APP751SL mice and in the APP751SLxPS1KI Ho doubles, the extracellular deposits of Aβ are observed mainly on either side of the layer of neurones in CA1. On the other hand, in CA1 (characterized by a pronounced effect on neurones all along the layer in the APP751SLxPS1KI Ho mice, FIGS. 7C and 7D), the Aβ immunolabeling with a granular appearance (corresponding to the abnormal intraneuronal accumulation of the Aβ peptide, see arrows) appears more intense in the APP751SLxPS1KI Ho mice. This is also true at 6 months old (see FIG. 8).

FIG. 8: Early onset of the process of neuronal death in CA1 in the APP751SLxPS1KI Ho mice. Plate illustrating the CA1 region of the hippocampus at 6 months old. The images represent, at high magnification in CA1, the Aβ immunolabeling in 3 APP751 mice (8A, 8B and 8C) and 3 APP751SLxPS1KI Ho mice (FIGS. 8G, 8H and 8I). They represent the Cresyl violet staining in the APP751 mice (FIGS. 8D, 8E and 8F) and the APP751SLxPS1KI Ho mice (8J, 8K and 8L). At 6 months old, the CA1 region of the hippocampus, in an APP751SLxPS1KI Ho mouse, is characterized by an already considerable number of extracellular deposits of Aβ (FIG. 8I), an intense intracellular granular labeling of Aβ (see arrows) and a loss of neurones stained with Cresyl violet associated with an increase in the number of glial type cells (FIG. 8L). For the other two APP751SLxPS1KI Ho mice, the layer of CA1 neurones stained with Cresyl violet appears to be hardly disorganized (FIG. 8J) or not at all (FIG. 8K). It should be noted that, for these two mice, the intracellular Aβ immunolabeling appears less intense and more diffuse (FIGS. 8G and 8H) than in the 3rd mouse (FIG. 8I).

EXAMPLES

Example 1

Construction of the Targeting Vector Carrying the Mutations M233T and L235P

The aim was to introduce two mutations into exon7 of the mouse PS1 gene, leading to alteration of residue M233 to T and residue L235 to P. The two new codons correspond to mutations identified in early onset Alzheimer patients (FAD).

A line of PS1 knock-in (PS1KI) mice was generated using a 2-step mutagenesis strategy similar to that described in Kwok et al. (1997 Neuroreport 8; 157-42) and Champion et al. (1996, Neuroreport 7, 1582-4).

The strategy was aimed at constructing a targeting vector carrying nucleic acid changes in codons 233 and 235 of the murine ps1 gene (see FIG. 1A).

Succinctly, a 17 kb genomic fragment of the mouse PS1 gene was isolated by screening a 129SvJ mouse genomic DNA library constructed in a lambda bacteriophage (Stratagene, catalogue # 946313). Analysis by digestion with restriction enzymes, sequencing, and comparison with the available partial sequences of the murine PS1 gene (Mitsuda et al. 1997, JBC 272, 23489-97) indicated that this fragment contained the region intron5 to exon 11 of the mouse PS1 gene. A 9.8 Kb BamHI-HindIII subfragment containing a portion of intron 5, exon 6, intron 6, exon 7 and a portion of intron 7 was subcloned into the plasmid pGEM-11Zf(+) (Promega, France) (FIG. 1A). The mutagenesis of the 2 codons was carried out using the Gene Editor kit (Promega) on the DNA fragment containing exon 7 and was confirmed by nucleotide sequencing.

The long (5') arm of the homologous recombination vector was obtained by cloning the 7 Kb BamHI-XbaI fragment containing exon 6. The short (3') arm was itself generated by subcloning the 1.8 Kb XbaI-EcoRI fragment containing exon 7 which has been subjected to mutagenesis. A positive selection cassette (pMCI-Neo cassette) was introduced into the XbaI site located in intron 6 at position −470 bp, positioned 5' of exon 7 (see FIG. 1A).

Example 2

Production of ES Cells Comprising PS1KI

The targeting vector, described in example 1, was linearized by digestion with NotI and electroporated into the embryonic stem (ES) cell line CK35 provided by Dr Charles Babinet, Pasteur Institute, Paris, France.

The cells were cultured as previously described (W. Wurtz and A. Joyner, Gene Targeting: A Practical Approach by Alexandra L. Joyner (Editor). Oxford University Press; 2nd edition (Feb. 15, 2000)).

430 cellular clones liable to be carrying the homologous recombination were selected in the presence of G418. The genomic DNA of these clones was analyzed by Southern blotting as previously described (Sambrook, Fritsch and Maniatis, Molecular Cloning; A Laboratory Manual, Cold Spring Harbor Laboratory Press, $2^{nd}$ edition, 1989) using a PS1 probe located outside the long arm recombination domain (FIG. 1A). Four cellular clones carrying the desired mutations in the PS1 gene could thus be identified. These cellular clones were used to establish a PS1KI transgenic mouse line.

Example 3

Construction of the PS1KI Mouse Line

The clone 18C5 was injected into blastocysts of C57B1/6 mice.

Five of the chimeric mice obtained showed transmission of the ps1 mutant allele to the germinal line (and therefore to their descendance).

From these founders, the PS1KI mouse line was established on a pure 129SV genetic background and on a mixed 129SV-C57B1/6 background.

The presence of the mutated PS1KI allele in the heterozygous (He) or homozygous (Ho) state was determined by Southern blotting with the 230 bp ps1 probe (FIG. 1B). The mutant mice are viable and fertile.

Example 4

Assaying of PS1 in the PS1KI Line

After euthanasia, the brain of the mice was removed and weighed. One hemisphere was conserved for immunohistochemistry (post-fixation) and the other was frozen and then homogenized individually on ice using a Potter homogenizer, in 2 ml of a buffer solution: 0.32 M sucrose, 4 mM Tris-HCl, pH 7.4, containing a cocktail of protease inhibitors (Complete™, Roche Diagnostics). The protein concentration was determined by the BCA method (Pierce). The homogenate was conserved at −80° C.

For the detection of PS1, 25 µg of brain protein extract were incubated at 56° C. for 20 min in Laemmli loading buffer containing 8M urea and 50 mM dithiothreitol. The proteins were fractionated by NuPAGE 4-12% Bis-Tris polyacrylamide gel electrophoresis (SDS-PAGE) in MES (2-(N-morpholino) ethanesulfonic acid) buffer. After transfer of the proteins onto a nitrocellulose filter (Amersham, France), the filter was heated in PBS for 5 min in order to increase the sensitivity, and immediately saturated with 5% (w/v) of powdered skimmed milk in a PBST (0.05% PBS (V/V), Tween 20) buffer for 1 h and incubated overnight at 4° C. with primary antibody in PBST buffer alone. Binding of the antibody was detected with an anti-IgG (anti-mouse) antibody conjugated to horseradish peroxidase (Amersham, France) at a dilution of 1/10,000 in PBST, followed by a system of detection by chemiluminescence (Amersham, France) according to the manufacturer's instructions. For the detection of PS1, the primary antibody MAB1563 (Chemicon, USA) was used at a 1/10,000 dilution. For the semi-quantitative analysis, the luminescence signals were digitized with a GeneGnome 16 bit CCD camera (Syngene, Cambridge, England) and analyzed with the Genetools software (Syngene). The linearity of the signal was verified by means of standard curves established with samples of 2.5 to 10 µg of homogenate per lane.

This analysis by immunoblotting made it possible to determine that the levels of expression of the C-terminal fragment of mutated PS1 remain normal and are not decreased in the PS1KI233/235 mouse (FIG. 1C).

Example 5

Production of the PS1KIxAPP Line by Crossing the PS1KI and APP Lines

PS1KI mice (described in examples 1 to 4) were crossed with a line of transgenic mice overexpressing the human form of the $APP_{751}$ cDNA carrying the Swedish (mutation K670N; M671L) and London (V717I) FAD mutations, under the control of the Thy-1 promoter. The mice overexpressing the human form of the $APP_{751}$ cDNA carrying the mutations were obtained as described in patent application WO 01/20977.

In all the following experiments, mice having the same genetic backgrounds were used to minimize any effect due to variations in genetic background.

Example 6

Assaying of the Total Aβ and Aβ42 Amyloid Peptide by the Immunoelectrochemiluminescence Method To quantify the overall pool of Aβ in the brain (soluble forms and aggregated or insoluble forms), aliquots of brain homogenate were treated with 2 volumes of a 9M solution of guanidine hydrochloride (GH) in 50 mM Tris, pH 7.4. The homogenates were mixed for 1 h, with 3 periods of sonication of 15 min, followed by centrifugation at 50 000 g at 4° C. for 2 h. The guanidine extracts were diluted to 1/20 in 20 mM Tris-HCl buffer, pH 7.6, containing 150 mM NaCl, 0.5% BSA (w/v) and 0.05% Tween 20 (w/v). The concentration of the Aβ peptide in the fractions was then determined by immunoelectrochemiluminescence (Yang et al., 1994, Biotechnology (NY) 12(2), 193-194) using 2 anti-Aβ peptide mouse monoclonal antibodies (4G8 and 6E10) and the Origen M8 Analyzer reader (IGEN Europe Inc. Oxford), following a protocol modified according to Khorkova et al. (*J. Neurosci. Methods* 82, 159-166 (1998)).

The monoclonal antibody 4G8 (Senetek PLC), which recognizes the residues 17-24 epitope of the Aβ peptide, is ruthenylated by means of the TAG-NHS ester according to the supplier's protocol (IGEN Europe Inc., Oxford). Ru-4G8 and the biotinylated antibody 6E10, epitope 1-10 of the Aβ peptide (Senetek PLC), are brought into contact with the soluble fraction of brain and the Ru-4G8/Aβ/6E10-biot tripartite complexes are quantified using the Origen reader. A range of synthetic peptide Aβ (Bachem) is used to calibrate each experiment. The amount of peptide Aβ is calculated in nanograms per g of initial weight of brain tissue.

To measure specifically the forms of Aβ peptide which end at position 42 (Aβ42), the antibody 6E10 was replaced with the monoclonal antibody 22F9, which binds specifically to the Aβ42 C-terminal end (Wirths et al., 2002, *Brain Pathol.* 12, 275-286).

In conclusion, the presence of the ps1 knock-in (PS1-KI) gene leads to:

An acceleration in the accumulation of Aβ (FIG. 2A) and Aβ42 (FIG. 2B) in the brain, with an even more pronounced effect when the PS1KI allele is present in the homozygous state (gene-dose effect). The effect of PS1KI(Ho) is more accentuated than with the transgenic mouse overexpressing PS1M146L previously described in application WO 01/20977.

A massive increase in the proportion of Aβ peptide exhibiting a β42 end, which represents the vast majority of the Aβ when the PS1KI mutation is in the homozygous state, as shown in FIG. 2C (Aβ42/total Aβ ratio equal to 0.92, at 2% months old, vs 0.25 in the absence of PS1KI and an intermediate value 0.70 in the presence of just one PS1KI allele: gene-dose effect). It is recognized in the literature that the species of Aβ peptide which finish at the β42 end represent the most pathological forms of the peptide. The PS1KIxAPP line therefore represents a model which is particularly enriched in pathological forms.

Example 7

Analysis of the Deposits of Aβ Peptide by Immunohistochemistry

For the immunohistochemistry/histology experiments, after having been removed and then post-fixed in 4% paraformaldehyde, the half-brains are cryoprotected overnight at 4° C. in a 0.2M sodium phosphate buffer ($NaH_2PO_4.2H_2O/Na_2HPO_4.12H_2O$, pH 7.4) containing 20% (P/V) sucrose. They are then frozen for 1 min in isopentane kept at a temperature of −30° C. in dry ice. 25 µm thick sections, cut on a cryostat thermostated at −30° C. (LEICA CM3000), are finally placed in a 0.02M PBS buffer and then conserved at 4° C.

Immunoenzymatic detection of the Aβ peptide was carried out, on these sections, by means of the revelation system involving the formation of avidin-biotin-peroxidase complexes (ABC) in which the horseradish peroxidase coupled to avidin is biotinylated. Briefly, after incubation for 30 min in blocking buffer (normal goat serum (Chemicon) at 10% in PBS containing 0.1% triton (Sigma)), the brain sections are placed in contact with a 0.3% $H_2O_2$ solution in order to eliminate the endoperoxidases present in the tissue. These sections are then incubated in the primary antibody solution containing 0.3% triton and 2% normal serum (overnight at 4° C.). The anti-Aβ primary antibody (4G8, Senetek) (monoclonal antibody directed against residues 17-24 of the Aβ peptide) used is biotinylated. After rinsing, the sections are therefore brought directly into contact with the ABC complex for 1 hour according to the manufacturer's instructions (Vectastin ABC Kit, Vector Laboratories, Burlingame, Calif.). 3,3'-Diaminobenzidine was used as chromogene for the peroxidase enzyme.

Thus, the acceleration of the abnormal accumulation of the Aβ peptide in the brain of the APP751SLxPS1KI Ho double transgenic mice, previously detected by biochemical assays on half-brain homogenates, was confirmed by immunohistochemistry. Specifically, microscopic analysis of the Aβ immunolabeling obtained on a half-brain section demonstrated the existence of an accelerated process of deposition of the Aβ peptide in the brain parenchyma of these mice. In fact, while the first deposits appear in the cortex and the hippocampus around the age of 6 months in the APP751SL mice (FIG. 3), they can be detected from the age of 2 months in the APP751SLxPS1KI double transgenics in the homozygous state. Compared to the APP751SL single transgenics, the density of the Aβ deposits is clearly greater in the hippocampus and in the cortex in the 6-month-old double transgenics (APP751SLxPS1KI Ho). In addition, the deposits are more widely distributed; in particular, deposits are already detected in the thalamus and also the pons (FIG. 3).

With age, in particular at 10 months old, the density and also the size of the deposits are increased in the brain of the APP751SL single transgenic mice (FIG. 4).

The distribution of these deposits is also broader since they are present in the thalamus. In the 10-month-old APP751SLxPS1KI Ho double transgenics, a similar progression of the process of deposition of the Aβ peptide is observed in the hippocampus, the cortex, the thalamus and the pons. The first deposits can be detected in a limited number in the striatum (FIG. 4). On the other hand, the cerebellum remains spared by the process of Aβ deposition. It should be noted that, in the brain of the 10-month-old PS1KI Ho mice (n=4), no deposition of the Aβ peptide is detected.

Example 8

Analysis of Neuronal Loss by Histology and Immunohistochemistry

The presence of a very high proportion of pathological Aβ42 peptide led to an analysis of whether, in the APP751SLxPS1KI Ho line, besides the acceleration of the process of deposition of the Aβ peptide, a neuronal loss develops with age. For this, 3 types of staining making it possible to visualize the disappearance of neuronal cells on brain tissue sections were carried out: a) histology with Cresyl violet, which stains the Niss1 bodies (cytoplasmic organelles associated with ribosomes of the rough endoplasmic reticulum) and makes it possible to demonstrate on brain sections all neuronal and glial cells; b) histology with methyl green, which stains the DNA of all cells; c) immunohistochemistry with BIP, which reveals the expression in the cells of a resident chaperone protein of the endoplasmic reticulum.

For the Cresyl violet staining, the brain tissue sections are mounted on gelatinized slides and then incubated for 10 minutes in a solution of Cresyl violet (C 1791, Sigma) at 0.5% in distilled water. After rinsing in acidic medium, the sections are finally dehydrated.

For the methyl green staining, the sections are mounted on gelatinized slides, incubated for 10 minutes in a solution of methyl green (M5015 from Sigma) at 1% in distilled water, rinsed, and then dehydrated.

For the BIP immunohistochemistry (polyclonal antibody, SPA-826, Stressgen), the protocol is identical to that applied for the Aβ peptide immunohistochemistry (see above), except for the additional incubation (1 h, ambient temperature) of the sections in a solution of biotinylated secondary antibody (anti-rabbit IgG antibody made in goat, Vector) before they are incubated in the ABC complex.

Microscopic analysis demonstrated, through the use of various histological/immunohistochemical markers, a decrease in the thickness of the pyramidal cell layer of the hippocampus, in particular of CA1, in the brain of the APP751SLxPS1KI Ho mice (n=3/3) (FIGS. 5 and 6). This decrease indicates the existence of a process of neuronal death which is already well established at the age of 10 months. At 6 months, neuronal death is present in the brain of ⅓ mice, suggesting the early onset of a neurotoxic process (FIG. 8). Analysis in parallel in the hippocampus, and in particular in CA1, of the 2 pathological processes, namely abnormal accumulation of the Aβ peptide in the brain and affected neurones, suggests a more probable role in the neurotoxic process of the intracellular accumulation of Aβ (phenomenon already described in the Thy-1APP751SLxPS1 M146L mice) than of its accumulation in extracellular deposits (FIG. 7). In fact, the neurones still present in CA1 exhibit an abnormally high expression of the Aβ peptide. In addition, the effect on neurones in CA1 is clearly present in regions lacking extracellular deposits. The existence of a probable gene-dose effect in the process of neuronal death in CA1 should be noted. An effect on neurones was also found in very old (>15 months) APP751SLxPS1KI mice having only one PS1KI allele.

The invention claimed is:

1. A transgenic mouse whose genome comprises a homozygous mutation in the endogenous presenilin 1 gene and an insertion of a nucleic acid sequence under the control of an exogenous Thy-1 promoter encoding a mutant Aβ peptide precursor protein (APP), wherein the amino acid sequence encoded by the presenilin 1 gene consists of the following two mutations a threonine residue at position 233 and a proline residue at position 235 of the murine presenilin 1 protein as set forth in SEQ ID No: 3;

wherein the amino acid sequence encoding the mutation in the human Aβ peptide precursor comprises human APP751 having Swedish (K670N/M671 L) and London (V7171) mutations; and wherein the transgenic mouse exhibits elevated Aβ protein levels, elevated Aβ 42levels, an Aβ 42 to total Aβ ratio greater than about 0.9, increased density of Aβ deposits, increased size of Aβ deposits, increased distribution of Aβ deposits, loss of neuronal cells and loss of glial cells.

2. A method for identifying a test compound useful for the treatment of elevated Aβ protein levels, elevated Aβ42 levels, elevated-Aβ42/Aβ ratio, increased density of Aβ deposits, increased size of Aβ deposits, increased distribution of Aβ deposits, loss of neuronal cells and loss of glial cells, comprising:

administering the test compound or a mixture of test compounds to the mouse of claim 1, and observing one or more of the characteristics exhibited by the transgenic mouse.

3. The mouse of claim 1, which expresses an amount of the encoded presenilin 1 protein equal to an amount of endogenous presenilin 1 protein expressed by a control individual of the same species of mouse, wherein the amount of each presenilin 1 protein expressed is determined by chemiluminescent detection of the peroxidase activity of an immunoblot with primary antibody MAB 1563 and secondary antibody anti-IgG anti-mouse conjugated to horseradish peroxidase.

* * * * *

UNITED STATES PATENT AND TRADEMARK OFFICE
CERTIFICATE OF CORRECTION

PATENT NO. : 7,700,823 B2  Page 1 of 1
APPLICATION NO. : 10/957311
DATED : April 20, 2010
INVENTOR(S) : Caty Casas Louzao et al.

It is certified that error appears in the above-identified patent and that said Letters Patent is hereby corrected as shown below:

In column 11, line 43, delete "Vectastin" and insert -- Vectastain --, therefor.

In column 12, line 22, delete "Niss1" and insert -- NissI --, therefor.

In column 23, line 39, in claim 1, delete "(V7171)" and insert -- (V717I) --, therefor.

In column 23, line 41, in claim 1, delete "42levels," and insert -- 42 levels, --, therefor.

Signed and Sealed this
Twenty-eighth Day of December, 2010

David J. Kappos
*Director of the United States Patent and Trademark Office*

SEQUENCE LISTING

<160> NUMBER OF SEQ ID NOS: 9

<210> SEQ ID NO 1
<211> LENGTH: 27
<212> TYPE: DNA
<213> ORGANISM: Artificial
<220> FEATURE:
<223> OTHER INFORMATION: Fragment of Murine PS1 Gene Containing Mutations

<400> SEQUENCE: 1
atcagtgccc tcacggcacc ggtattt                                       27

<210> SEQ ID NO 2
<211> LENGTH: 9
<212> TYPE: PRT
<213> ORGANISM: Artificial
<220> FEATURE:
<223> OTHER INFORMATION: Amino Acid Sequence Corresponding to SEQ. ID No. 1

<400> SEQUENCE: 2

Ile Ser Ala Leu Thr Ala Pro Val Phe
1               5

<210> SEQ ID NO 3
<211> LENGTH: 467
<212> TYPE: PRT
<213> ORGANISM: Artificial
<220> FEATURE:
<223> OTHER INFORMATION: Murine PS1 Protein with Mutations M233T and L235P

<400> SEQUENCE: 3

Met Thr Glu Ile Pro Ala Pro Leu Ser Tyr Phe Gln Asn Ala Gln Met
1               5                   10                  15

Ser Glu Asp Ser His Ser Ser Ser Ala Ile Arg Ser Gln Asn Asp Ser
                20                  25                  30

Gln Glu Arg Gln Gln Gln His Asp Arg Gln Arg Leu Asp Asn Pro Glu
            35                  40                  45

Pro Ile Ser Asn Gly Arg Pro Gln Ser Asn Ser Arg Gln Val Val Glu
        50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Val Thr Val Ala Leu Leu Ile Trp Asn Phe Gly Val Val

```
            195                 200                 205
Gly Met Ile Ala Ile His Trp Lys Gly Pro Leu Arg Leu Gln Gln Ala
    210                 215                 220

Tyr Leu Ile Met Ile Ser Ala Leu Thr Ala Pro Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
    290                 295                 300

Ala Gln Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Gly Ser Ile
            355                 360                 365

Leu Thr Ser Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
    450                 455                 460

Phe Tyr Ile
465

<210> SEQ ID NO 4
<211> LENGTH: 27
<212> TYPE: DNA
<213> ORGANISM: Mus musculus

<400> SEQUENCE: 4
atcagtgccc tcatggccct ggtattt                                           27

<210> SEQ ID NO 5
<211> LENGTH: 9
<212> TYPE: PRT
<213> ORGANISM: Mus musculus

<400> SEQUENCE: 5

Ile Ser Ala Leu Met Ala Leu Val Phe
1               5

<210> SEQ ID NO 6
<211> LENGTH: 2265
<212> TYPE: DNA
<213> ORGANISM: Homo sapiens
```

<400> SEQUENCE: 6

```
cccgggtcca ccatgctgcc cggtttggca ctgctcctgc tggccgcctg gacggctcgg      60
gcgctggagg tacccactga tggtaatgct ggcctgctgg ctgaacccca gattgccatg     120
ttctgtggca gactgaacat gcacatgaat gtccagaatg ggaagtggga ttcagatcca     180
tcagggacca aaacctgcat tgataccaag gaaggcatcc tgcagtattg ccaagaagtc     240
taccctgaac tgcagatcac caatgtggta gaagccaacc aaccagtgac catccagaac     300
tggtgcaagc ggggccgcaa gcagtgcaag acccatcccc actttgtgat tccctaccgc     360
tgcttagttg gtgagtttgt aagtgatgcc cttctcgttc ctgacaagtg caaattctta     420
caccaggaga ggatggatgt ttgcgaaact catcttcact ggcacaccgt cgccaaagag     480
acatgcagtg agaagagtac caacttgcat gactacggca tgttgctgcc ctgcggaatt     540
gacaagttcc gagggtaga gtttgtgtgt tgcccactgg ctgaagaaag tgacaatgtg     600
gattctgctg atgcggagga ggatgactcg gatgtctggt ggggcggagc agacacagac     660
tatgcagatg ggagtgaaga caaagtagta gaagtagcag aggaggaaga gtggctgag      720
gtggaagaag aagaagccga tgatgacgag gacgatgagg atggtgatga ggtagaggaa     780
gaggctgagg aacccctacga agaagccaca gagagaacca ccagcattgc caccaccacc    840
accaccacca cagagtctgt ggaagaggtg gttcgagagg tgtgctctga acaagccgag     900
acggggccgt gccgagcaat gatctcccgc tggtactttg atgtgactga agggaagtgt     960
gccccattct tttacggcgg atgtggcggc aaccggaaca cttttgacac agaagagtac    1020
tgcatggccg tgtgtggcag cgccattcct acaacagcag ccagtacccc tgatgccgtt    1080
gacaagtatc tcgagacacc tggggatgag aatgaacatg cccatttcca gaaagccaaa    1140
gagaggcttg aggccaagca ccgagagaga atgtcccagg tcatgagaga atgggaagag    1200
gcagaacgtc aagcaaagaa cttgcctaaa gctgataaga aggcagttat ccagcatttc    1260
caggagaaag tggaatcttt ggaacaggaa gcagccaacg agagacagca gctggtggag    1320
acacacatgg ccagagtgga agccatgctc aatgaccgcc gccgcctggc cctggagaac    1380
tacatcaccg ctctgcaggc tgttcctcct cggcctcgtc acgtgttcaa tatgctaaag    1440
aagtatgtcc gcgcagaaca gaaggacaga cagcacaccc taaagcattt cgagcatgtg    1500
cgcatggtgg atcccaagaa agccgctcag atccggtccc aggttatgac acacctccgt    1560
gtgatttatg agcgcatgaa tcagtctctc tccctgctct acaacgtgcc tgcagtggcc    1620
gaggagattc aggatgaagt tgatgagctg cttcagaaag agcaaaacta ttcagatgac    1680
gtcttggcca acatgattag tgaaccaagg atcagttacg aaacgatgc tctcatgcca     1740
tctttgaccg aaacgaaaac caccgtggag ctccttcccg tgaatggaga gttcagcctg    1800
gacgatctcc agccgtggca ttcttttggg gctgactctg tgccagccaa cacagaaaac    1860
gaagttgagc ctgttgatgc ccgccctgct gccgaccgag gactgaccac tcgaccaggt    1920
tctgggttga caaatatcaa gacgaggag atctctgaag tgaatctgga tgcagaattc    1980
cgacatgact caggatatga agttcatcat caaaaattgg tgttctttgc agaagatgtg    2040
ggttcaaaca aaggtgcaat cattggactc atggtgggcg tgttgtcat agcgacagtg     2100
atcatcatca ccttggtgat gctgaagaag aaacagtaca catccattca tcatggtgtg    2160
gtggaggttg acgccgctgt cacccccgag gagcgccacc tgtccaagat gcagcagaac    2220
ggctacgaaa atccaaccta caagttcttt gagcagatgc agaac                    2265
```

<210> SEQ ID NO 7
<211> LENGTH: 751
<212> TYPE: PRT
<213> ORGANISM: Homo sapiens

<400> SEQUENCE: 7

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Ile Pro Thr Thr Ala Ala Ser Thr
        340                 345                 350

Pro Asp Ala Val Asp Lys Tyr Leu Glu Thr Pro Gly Asp Glu Asn Glu
    355                 360                 365

His Ala His Phe Gln Lys Ala Lys Glu Arg Leu Glu Ala Lys His Arg
370                 375                 380
```

Glu Arg Met Ser Gln Val Met Arg Glu Trp Glu Ala Glu Arg Gln
385                 390                 395                 400

Ala Lys Asn Leu Pro Lys Ala Asp Lys Lys Ala Val Ile Gln His Phe
            405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
            435                 440                 445

Arg Arg Arg Leu Ala Leu Glu Asn Tyr Ile Thr Ala Leu Gln Ala Val
450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
            485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
            515                 520                 525

Leu Tyr Asn Val Pro Ala Val Ala Glu Glu Ile Gln Asp Glu Val Asp
545                 550                 555                 560

Glu Leu Leu Gln Lys Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
            565                 570                 575

Ser Leu Thr Glu Thr Lys Thr Thr Val Glu Leu Leu Pro Val Asn Gly
            580                 585                 590

Glu Phe Ser Leu Asp Asp Leu Gln Pro Trp His Ser Phe Gly Ala Asp
            595                 600                 605

Ser Val Pro Ala Asn Thr Glu Asn Glu Val Glu Pro Val Asp Ala Arg
            610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Asn Leu Asp Ala Glu Phe
            645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
            675                 680                 685

Gly Gly Val Val Ile Ala Thr Val Ile Ile Thr Leu Val Met Leu
690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
            725                 730                 735

Gly Tyr Glu Asn Pro Thr Tyr Lys Phe Phe Glu Gln Met Gln Asn
            740                 745                 750

<210> SEQ ID NO 8
<211> LENGTH: 221
<212> TYPE: DNA
<213> ORGANISM: Artificial
<220> FEATURE:
<223> OTHER INFORMATION: Murine PS1 Exon 7 Containing Mutations

<400> SEQUENCE: 8

```
                                          -continued ggaagtattt aagacctaca atgtcgccgt ggactacgtt acagtagcac tcctaatctg     60
gaattttggt gtggtcggga tgattgccat ccactggaaa ggcccccttc gactgcagca    120
ggcgtatctc attatgatca gtgccctcac ggcaccggta tttatcaagt acctccccga    180
atggaccgca tggctcatct tggctgtgat ttcagtatat g                        221

<210> SEQ ID NO 9
<211> LENGTH: 221
<212> TYPE: DNA
<213> ORGANISM: Mus musculus

<400> SEQUENCE: 9
ggaagtattt aagacctaca atgtcgccgt ggactacgtt acagtagcac tcctaatctg     60
gaattttggt gtggtcggga tgattgccat ccactggaaa ggcccccttc gactgcagca    120
ggcgtatctc attatgatca gtgccctcat ggccctggta tttatcaagt acctccccga    180
atggaccgca tggctcatct tggctgtgat ttcagtatat g                        221
```